United States Patent
Masago

(10) Patent No.: US 10,286,734 B2
(45) Date of Patent: May 14, 2019

(54) METHOD AND APPARATUS FOR ESTIMATING UNEVEN TIRE WEAR

(71) Applicant: BRIDGESTONE CORPORATION, Tokyo (JP)

(72) Inventor: Takeshi Masago, Tokyo (JP)

(73) Assignee: BRIDGESTONE CORPORATION, Chuo-ku, Tokyo (JP)

( * ) Notice: Subject to any disclaimer, the term of this patent is extended or adjusted under 35 U.S.C. 154(b) by 204 days.

(21) Appl. No.: 15/037,192

(22) PCT Filed: Jul. 31, 2014

(86) PCT No.: PCT/JP2014/070177
§ 371 (c)(1),
(2) Date: May 17, 2016

(87) PCT Pub. No.: WO2015/079741
PCT Pub. Date: Jun. 4, 2015

(65) Prior Publication Data
US 2016/0280014 A1 Sep. 29, 2016

(30) Foreign Application Priority Data
Nov. 26, 2013 (JP) ................ 2013-243729

(51) Int. Cl.
*G01M 17/02* (2006.01)
*G01N 29/44* (2006.01)
*B60C 11/24* (2006.01)

(52) U.S. Cl.
CPC .......... *B60C 11/243* (2013.01); *B60C 11/246* (2013.01); *G01M 17/025* (2013.01);
(Continued)

(58) Field of Classification Search
CPC .. B60C 11/243; B60C 11/246; G01M 17/025; G01N 29/4436; G01N 2291/0235; G01N 2291/0289
See application file for complete search history.

(56) References Cited

U.S. PATENT DOCUMENTS 8,483,976 B2 * 7/2013 Morinaga ............... B60C 11/24
  702/189
2003/0192375 A1  10/2003 Sugai et al.
(Continued)

FOREIGN PATENT DOCUMENTS

EP  2172760 A1  4/2010
EP  2301769 A1  3/2011
(Continued)

OTHER PUBLICATIONS

Communication dated Oct. 11, 2016, from the European Patent Office in counterpart European Application No. 14865056.7.
(Continued)

*Primary Examiner* — Matthew G Marini
(74) *Attorney, Agent, or Firm* — Sughrue Mion, PLLC

(57) ABSTRACT

A method and an apparatus for estimating uneven wear in the tire shoulder with high accuracy using a fewer number of sensors are provided. An uneven tire wear estimating apparatus includes an acceleration sensor (11) disposed on an inner surface of a tire tread for measuring radial acceleration, an acceleration waveform extracting means (12) for extracting an acceleration waveform in a post-trailing-end domain from output signals of the acceleration sensor, means for calculating a vibration level α of an uneven wear measured band and a vibration level β of a reference band from the extracted acceleration waveform, an uneven wear determination index calculating means (16) for calculating an uneven wear determination index γ, which is an index for determining au uneven wear, from the vibration level α and
(Continued)

the vibration level β, and a determining means (18) for determining whether an uneven wear is occurring in an edge of the tire shoulder from the value of the uneven wear determination index γ.

5 Claims, 5 Drawing Sheets

(52) U.S. Cl.
CPC . *G01N 29/4436* (2013.01); *G01N 2291/0235* (2013.01); *G01N 2291/0289* (2013.01)

(56) References Cited

U.S. PATENT DOCUMENTS

| | | | |
|---|---|---|---|
| 2005/0085987 A1* | 4/2005 | Yokota | B60C 23/0477 701/80 |
| 2007/0255510 A1* | 11/2007 | Mancosu | B60T 8/172 702/34 |
| 2008/0027658 A1 | 1/2008 | Ichikawa et al. | |
| 2010/0186492 A1* | 7/2010 | Morinaga | B60C 11/24 73/146 |
| 2010/0199756 A1 | 8/2010 | Hanatsuka | |
| 2011/0118989 A1 | 5/2011 | Morinaga | |

FOREIGN PATENT DOCUMENTS

| | | |
|---|---|---|
| JP | 2007-153034 A | 6/2007 |
| JP | 2008132921 A | 6/2008 |
| JP | 2009-018667 A | 1/2009 |
| JP | 2009-019950 A | 1/2009 |
| JP | 2010159031 A | 7/2010 |
| JP | 2013-136297 A | 7/2013 |
| JP | 2013-169816 A | 9/2013 |
| WO | 2009/008319 A1 | 1/2009 |
| WO | 2009/008502 A1 | 1/2009 |
| WO | 2009027233 A1 | 3/2009 |
| WO | 2009/157516 A1 | 12/2009 |
| WO | 2010046872 A1 | 4/2010 |
| WO | 2013/175871 A1 | 11/2013 |

OTHER PUBLICATIONS

International Preliminary Report on Patentability issued from the International Bureau in counterpart application No. PCT/JP2014/070177, dated Jun. 9, 2016.
Abstract of JP 2013136297 A published Jul. 11, 2013.
International Search Report for PCT/JP2014/070177 dated Nov. 4, 2014 [PCT/ISA/210].
Written Opinion for PCT/JP2014/070177 dated Nov. 4, 2014 [PCT/ISA/237].
Communication dated Sep. 28, 2017 from the State Intellectual Property Office of the P.R.C. in counterpart Chinese application No. 201480064739.7.

* cited by examiner

METHOD AND APPARATUS FOR ESTIMATING UNEVEN TIRE WEAR

CROSS REFERENCE TO RELATED APPLICATIONS

This application is a National Stage of International Application No. PCT/JP2014/070177 filed Jul. 31, 2014, claiming priority based on Japanese Patent Application No. 2013-243729 filed Nov. 26, 2013, the contents of all of which are incorporated herein by reference in their entirety.

BACKGROUND OF THE INVENTION

1. Field of the Invention

The present invention relates to a method and apparatus for estimating whether an uneven wear is occurring in an edge of the tire shoulder from output signals of an acceleration sensor disposed on an inner surface side of the tire tread.

2. Description of the Related Art

A tire gets worn in the tread surface as it runs from having friction with the road surface. From the viewpoint of tire performance, it is desirable that the tread surface wears away evenly, thus causing no significant change in the shape of the contact patch (footprint). However, at the time of cornering, acceleration, or deceleration, lateral or fore-aft forces in relation to the traveling direction of the vehicle may work on tires. As a result, there occur differences in the amount of wear between the central part and the shoulder parts of the tire tread.

As these uneven wears accumulate, a tire may have an extremely worn edge of the tire shoulder. The tire with an advanced uneven wear like this is called an unevenly worn tire in contrast to an evenly worn tire which has an evenly worn surface of the tread.

A tire having an extreme uneven wear, if it keeps on being used continuously, may eventually fail to deliver its primary performance. Especially with winter tires, a problem that frequently arises is a lost grip on the road surface.

Also, an unevenly worn tire has a shape of the contact patch that is deviant from ideal. Hence, such a tire will experience a greater loss of fuel economy performance than a normally worn tire having an evenly worn tread surface.

There has been a method known in the art in which an acceleration sensor is disposed at each of the axial center and shoulder portions on an inner surface side of the tire tread. And using the output signals from these acceleration sensors, estimation is made whether an uneven wear is occurring in an edge of the tire shoulder (see Patent Document 1, for instance). More specifically, a differentiated acceleration waveform at the axial center and differentiated acceleration waveforms at the shoulder portions are obtained by differentiating each of the radial acceleration waveforms at the axial center and the shoulders detected by the respective acceleration sensors. Then a differentiated peak value ratio is calculated, which is a ratio between the differentiated peak value at the center and the differentiated peak value at the shoulder, both being the peak values at tire contact ends calculated from the respective differentiated acceleration waveforms. Now the calculated differentiated peak value ratio is compared with the differentiated peak value ratio having been calculated in advance of a tire without the presence of uneven wear in an edge of the shoulder portion to determine whether an uneven wear is occurring in an edge of the tire shoulder.

As described above, according to Patent Document 1, the uneven wear in the tire shoulder is estimated using the ratio between the differentiated peak value at the center and that at the shoulder calculated respectively from the output signals of the acceleration sensors disposed at the axial center and the shoulder portions on an inner surface side of the tire tread. Thus drops in accuracy in estimating an uneven wear due to changes in the traveling speed of the vehicle can be avoided.

CONVENTIONAL ART DOCUMENT

Patent Document

Patent Document 1: Japanese Unexamined Patent Application No. 2013-136297

SUMMARY OF THE INVENTION

Problem to be Solved by the Invention

However, the system as disclosed in Patent Document 1 requires the use of at least three acceleration sensors. With an increase in the number of acceleration sensors, various problems may arise such as rising cost, increased amount of data to be processed, and degraded reliability from maintenance point of view.

Thus it is desired that a technique be developed to enhance the accuracy of estimating uneven wear in the tire shoulder while reducing the number of sensors.

The present invention has been made to solve the foregoing problems, and an object of the invention is to provide a method and apparatus for estimating uneven wear in the tire shoulder with accuracy using a fewer number of sensors.

Means for Solving the Problem

As a result of an earnest investigation by the present inventor, it has been discovered that the vibration level of a specific frequency range (800 to 1200 Hz) of the acceleration waveform in the post-trailing-end domain of the radial acceleration waveform shows significant variations with the changes in the uneven wear status in an edge of the tire shoulder. And the vibration level of the specific frequency range (hereinafter referred to as "uneven wear measured band") is calculated, and the vibration level of the uneven wear measured band is compared with a frequency range, where there is little noise and the vibration level is little affected by changes in the uneven wear status in the edge of the tire shoulder, (hereinafter referred to as "reference band"). And this reference vibration level can be used as a measure in estimating the uneven wear. Thus, the inventor has come up with the present invention that can detect changes in uneven wear status with certainty using a fewer number of sensors and can reduce the effect of changes in the traveling speed of the vehicle significantly.

That is, the present invention relates to a method for estimating uneven tire wear from a radial acceleration waveform detected by an acceleration sensor. The method includes the steps of: (a) extracting a radial acceleration waveform in a post-trailing-end domain from output signals of the acceleration sensor disposed on an inner surface of the tire tread during vehicular travel, (b) calculating a measured vibration level $\alpha$, which is a level of acceleration in the frequency band of 800 to 1200 Hz, from the extracted acceleration waveform, (c) calculating a reference vibration level $\beta$, which is a level of acceleration in the frequency band of 2000 to 2400 Hz, from the extracted acceleration waveform, (d) calculating an uneven wear determination index γ, which is an index for determining uneven tire wear, from the measured vibration level α and the reference vibration level β, and (e) determining whether an uneven wear is occurring in an edge of the tire shoulder from the value of the calculated uneven wear determination index γ.

In this manner, the vibration level of the uneven wear measured band where the vibration level varies greatly with changes in uneven wear status in an edge of the tire shoulder is compared with the vibration level of the reference band, where there is little noise and the vibration level is little affected by changes in the uneven wear status in the edge of the tire shoulder. And an index which can be used as a measure in determining the uneven wear is calculated, and this index is used to determine whether an uneven wear is occurring in the edge of the tire shoulder. As a result, changes in uneven wear status can be estimated with certainty using a fewer number of sensors, and the effect of changes in the traveling speed of the vehicle can be lessened significantly.

It is to be noted that the acceleration waveform in the post-trailing-end domain to be used is, for instance, an output signal waveform after the point (trailing end point) where the location of the acceleration sensor leaves the road surface, and at the same time up to the point where the level of the post-trailing-end domain output signals drops below a predetermined signal level, out of the output signals of the acceleration sensor during vehicular travel. Or the waveform up to the time domain of about ⅕ to ⅔ of one tire revolution from the trailing-end point may be used.

Also, the edge of the tire shoulder meant herein is an edge portion on the axially outer side of the tread and in the land portion located outside of the circumferential groove located axially outward in the tread.

Also, according to the present invention, the uneven wear determination index $\gamma = \alpha/\beta$.

Thus, the uneven wear determination index γ, which can eliminate the effect of traveling speed by a simple calculation, can be calculated.

Also, in step (e), the uneven wear determination index γ is compared with a threshold value obtained in advance or a reference determination index $\gamma_0$, which is an uneven wear determination index obtained in advance of a normal tire without an uneven wear occurring, to determine whether an uneven wear is occurring in an edge of the tire shoulder. Hence, it is possible to estimate an uneven wear in the edge of the tire shoulder with even greater accuracy.

Also, the present invention relates to an uneven tire wear estimating apparatus for estimating uneven tire wear from the radial acceleration detected by an acceleration sensor. The uneven tire wear estimating apparatus includes an acceleration sensor disposed on an inner surface of a tire tread for measuring acceleration in the radial direction of the tire, an acceleration waveform extracting means for extracting an acceleration waveform in a post-trailing-end domain from output signals of the acceleration sensor, an uneven wear measured band value calculating means for calculating a measured vibration level α, which is a level of acceleration in the frequency band of 800 to 1200 Hz, from the extracted acceleration waveform, a reference band value calculating means for calculating a reference vibration level β, which is a level of acceleration in the frequency band of 2000 to 2400 Hz, from the extracted acceleration waveform, an uneven wear determination index calculating means for calculating an uneven wear determination index γ, which is an index for determining uneven wear, from the measuring vibration level α and the reference vibration level β, and a determining means for determining whether an uneven wear is occurring in an edge of the tire shoulder from the value of the calculated uneven wear determination index γ.

By implementing the above-described structure, it is possible to realize an uneven tire wear estimating apparatus that can estimate with accuracy uneven wear in the edge of the tire shoulder by a fewer number of sensors.

It is to be noted that the foregoing summery of the invention does not recite all the necessary features of the invention and hence any subcombinations of the described features should be understood to fall within the scope of the invention.

BEST MODE FOR CARRYING OUT THE INVENTION

Figure 1:
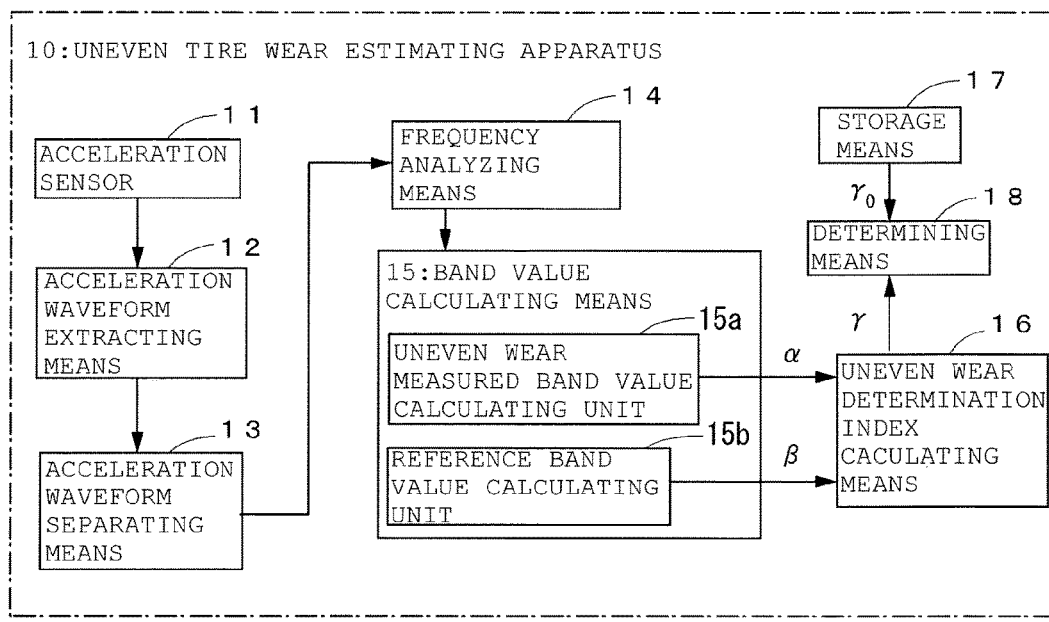
FIG. 1 is a block diagram showing a constitution of an uneven tire wear estimating apparatus according to a preferred embodiment.
Figure 2:
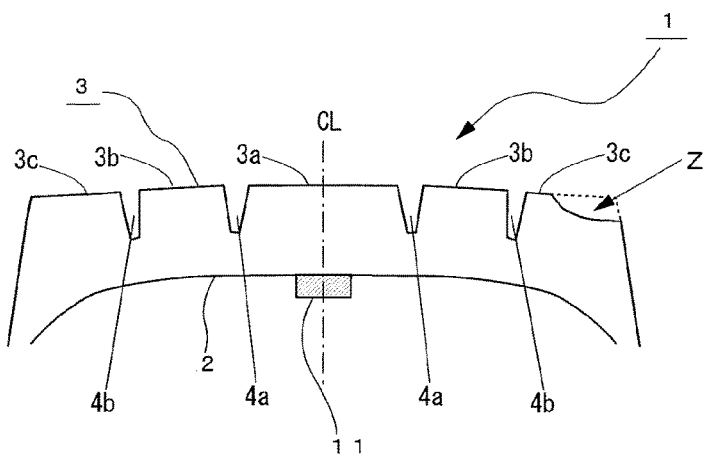
FIG. 2 is an illustration showing an example of installation of an acceleration sensor.

FIG. 1 is a functional block diagram showing a constitution of an uneven tire wear estimating apparatus 10. The uneven tire wear estimating apparatus 10 includes an acceleration sensor 11, an acceleration waveform extracting means 12, an acceleration waveform separating means 13, a frequency analyzing means 14, a band value calculating means 15, an uneven wear determination index calculating means 16, a storage means 17, and a determining means 18 to estimate whether an uneven (uneven or irregular) wear is occurring in an edge of the tire shoulder. An edge of the tire shoulder meant here, in an example of a tire 1 in FIG. 2, refers to an edge in an axially outer portion of the land (shoulder land) 3c defined by a shoulder groove 4b located in an axially outer position of the circumferential grooves 4a and 4b formed in the tire tread. It is to be noted that, in FIG. 2, reference numeral 3a refers to the central land defined by the two circumferential grooves 4a, 4a, and reference numeral 3b refers to an outer land defined by the circumferential grooves 4a, 4b. Also, the uneven wear in an edge of the tire shoulder refers to a status of rubber loss due to wear in an edge of the tire shoulder as indicated by Z in the figure. Hereinafter, the uneven wear is referred to as the shoulder edge wear.

The acceleration sensor 11 is disposed at the axial center indicated by CL in the figure on the inner liner 2 of the tire 1 in such a manner that the detection direction is the radial direction of the tire. And the acceleration sensor 11 detects radial acceleration being inputted to the central portion of the tire tread 3.

The acceleration sensor 11 constitutes the sensor unit of the uneven tire wear estimating apparatus 10, whereas the respective means from the acceleration waveform extracting means 12 through the determining means 18 constitute the storage and computing units thereof.

The means constituting the storage and computing units may, for instance, be constituted by software for the computer and disposed on the not-shown vehicle body side. It is to be noted that the storage means 17 is constituted by a memory such as a RAM.

Also, the arrangement to be employed for the transmission of output signals of the acceleration sensor 11 to the computing units is preferably by installing an amplifier and transmitter on the tire inside or on the not-shown wheel, for instance. And the output signals of the acceleration sensor 11 are wirelessly transmitted to the vehicle body side after being amplified. Also, the arrangement may be such that the storage and computing units are disposed on the tire side and the determination results of the determining means 18 are transmitted to the not-shown vehicle control unit on the vehicle body side.

The acceleration waveform extracting means 12 extracts a radial acceleration waveform, which is a time-series waveform in the radial direction of the tire near the tire contact patch, from the output signals of the acceleration sensor 11.

The acceleration waveform separating means 13 separates and extracts an acceleration waveform in the post-trailing-end domain (hereinafter referred to as the post-trailing-end waveform) from the radial acceleration waveform extracted by the acceleration waveform extracting means 12.

Figure 3:
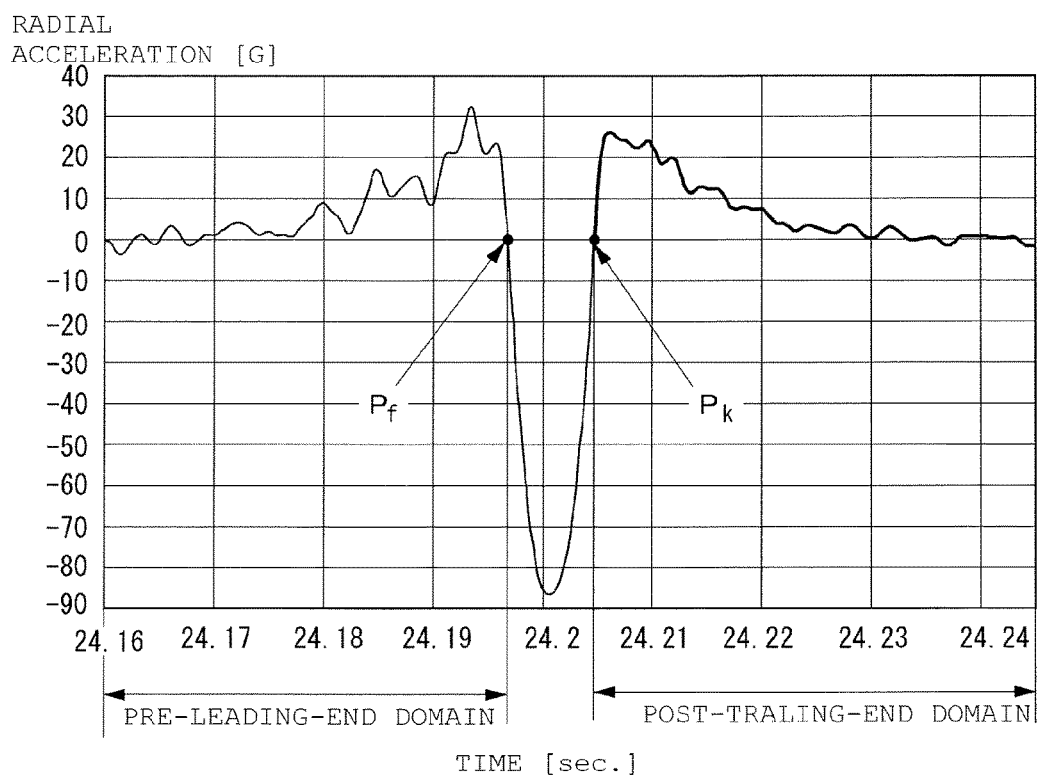
FIG. 3 is a diagram showing an example of acceleration in the radial direction of the tire.

FIG. 3 is a diagram showing an example of radial acceleration waveform detected by the acceleration sensor 11. The horizontal axis of the diagram represents time in [sec.], and the vertical axis the level of radial acceleration in [G]. The output signals of the acceleration sensor 11 during vehicular travel are zero (0) at the point where the installation point of the acceleration sensor 11 comes in contact with the road surface (more precisely the tread surface at the position radially outside of the installation point of the acceleration sensor 11) (leading-end point) $P_f$ and the point where it leaves the road surface (trailing-end point) $P_k$. The acceleration waveform separating means 13 separates only the acceleration waveform in the time domain after the trailing-end point $P_k$ (post-trailing-end domain) from the radial acceleration waveform and sends it as the post-trailing-end waveform to the frequency analyzing means 14.

It is to be noted that the positions of the leading-end point $P_f$ and the trailing-end point $P_k$ are identified respectively from the positions of the two peak values of differentiated acceleration waveform obtained by differentiating the above-mentioned radial acceleration waveform.

Also, in the present embodiment, the post-trailing-end domain is the time domain from the trailing-end point $P_k$ to 30% of one tire revolution from the trailing-end point $P_k$.

The frequency analyzing means 14, which is constituted by a frequency analyzing unit, such as an FFT analyzer, obtains a frequency spectrum of post-trailing-end waveform by applying an FFT processing to the post-trailing-end waveform extracted by the acceleration waveform separating means 13.

Figure 4:
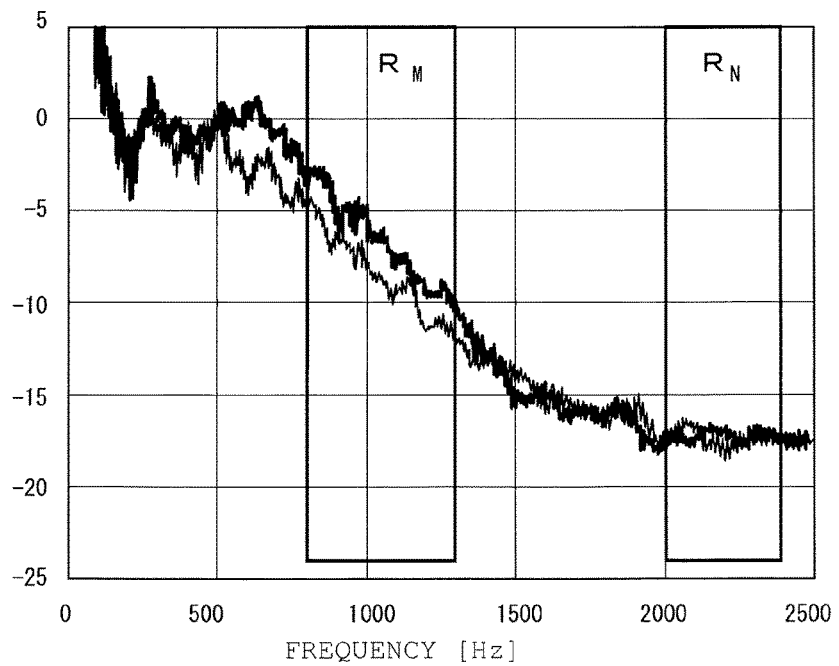
FIG. 4 is a diagram showing an example of a frequency spectrum of radial acceleration in a post-trailing-end domain.

FIG. 4 is a diagram showing examples of frequency spectrums of post-trailing-end waveforms. The horizontal axis of the diagram represents frequency in [Hz], and the vertical axis the level of radial acceleration (acceleration spectrum level) in [dB]. The thick solid line in the diagram stands for the data of a tire having a shoulder edge wear (hereinafter referred to as unevenly worn tire), whereas the thin solid line stands for the data of a tire having no shoulder edge wear (hereinafter referred to as normally worn tire).

Figure 5:
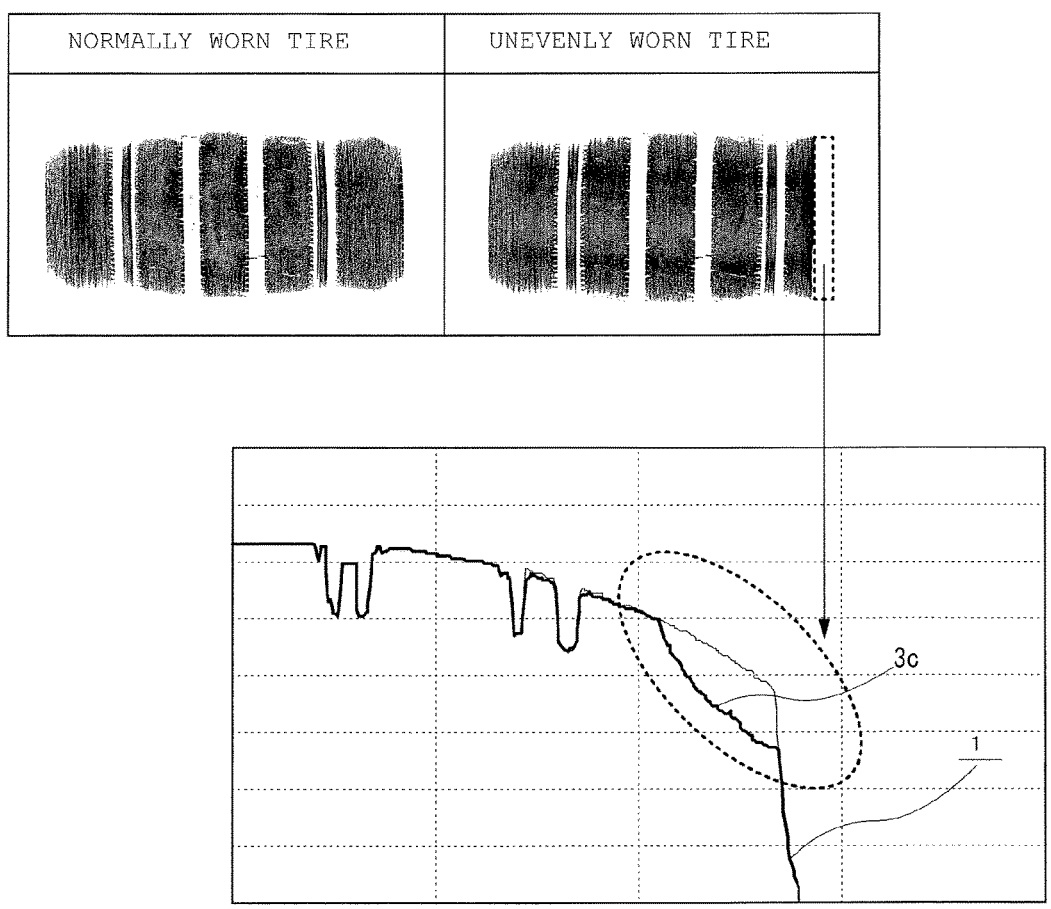
FIG. 5 is an illustration showing a status of a shoulder edge wear.

The unevenly worn tire is a tire having a status of lost rubber due to excessive wear in an axially outer edge of a shoulder land 3c as indicated by the thick line in FIG. 5. On the other hand, the normally worn tire has a wear as indicated by the thin line in the figure, but it has no excessive loss of rubber as that of the unevenly worn tire. It is to be noted that the tire illustrated in FIG. 5 is the same tire as used in the actual vehicle test to be discussed later.

As shown in FIG. 4, the acceleration spectrum level of the unevenly worn tire is higher than that of the normally worn tire in the frequency range of 800 to 1200 Hz indicated by $R_M$ (uneven wear measured band). On the other hand, the acceleration spectrum level of the unevenly worn tire is nearly equal to that of the normally worn tire in the frequency range of 2000 to 2400 Hz indicated by $R_N$ (reference band).

The band value calculating means 15 is provided with an uneven wear measured band value calculating unit 15a and a reference band value calculating unit 15b. And the band value calculating means 15 calculates the R.M.S value of the acceleration spectrum level in the uneven wear measured band (measured vibration level) α and the R.M.S value of the acceleration spectrum level in the reference band (reference vibration level) β from the frequency spectrum of the post-trailing-end waveform calculated by the frequency analyzing means 14.

The uneven wear determination index calculating means 16 calculates an uneven wear determination index γ, which is an index for determining whether a shoulder edge wear is occurring or not, using the measured vibration level α and reference vibration level β calculated by the band value calculating means 15. In the present embodiment, γ=α/β.

The storage means 17 stores a reference determination index $γ_0$, which is an uneven wear determination index obtained in advance by operating a vehicle fitted with normally worn tires.

The determining means 18 determines whether a shoulder edge wear is occurring or not by comparing the uneven wear determination index γ calculated by the uneven wear determination index calculating means 16 against the reference determination index $γ_0$.

Now, a description is given of a method for estimating uneven tire wear.

First, a time-series waveform of radial acceleration at the center of the inner liner 2 deforming along with the deformation of the tire tread 3 is detected by the acceleration sensor 11.

Next, a radial acceleration waveform is extracted by the acceleration waveform extracting means 12. Then a post-trailing-end waveform is separated and extracted from the radial acceleration waveform by the acceleration waveform separating means 13. And a frequency spectrum of the post-trailing-end waveform is derived by the frequency analyzing means 14.

As shown in FIG. 4, the acceleration spectrum level of the unevenly worn tire is higher than that of the normally worn tire in the uneven wear measured band indicated by $R_M$, whereas the acceleration spectrum level of the unevenly worn tire is nearly equal to that of the normally worn tire in the reference band indicated by $R_N$. Thus, the measured vibration level α, which is the vibration level of the uneven wear measured band, and the reference vibration level β, which is the vibration level of the reference band, are calculated from the frequency spectrum of the post-trailing-end waveform by the band value calculating means 15. Then the ratio between these, $\gamma=\alpha/\beta$, is calculated, and it is used as an uneven wear determination index $\gamma$, which is an index for determining whether a shoulder edge wear is occurring or not.

Then the calculated uneven wear determination index $\gamma$ is compared with the reference determination index $\gamma_0$ stored in the storage means 17 to determine whether a shoulder edge wear is occurring or not. The determination can be made, for instance, by calculating $\Delta=\gamma-\gamma_0$. And when $\Delta$ is in excess of the threshold value $\Delta_k$ which has been set in advance, it is determined that the shoulder edge wear is actually occurring. Or when $\Delta$ is equal to or less than the threshold value $\Delta_k$, then it is determined that no shoulder edge wear is occurring.

EXAMPLE

A vehicle fitted with a test tire having an acceleration sensor disposed at the axial center on the inner liner was prepared. The acceleration sensor was so disposed to have the detection direction in the radial direction of the tire. While the vehicle was operated at speeds of 60 km/hr to 80 km/hr, the radial acceleration waveforms and the frequency spectrums of the post-trailing-end waveforms were obtained by the storage and computing units mounted on the vehicle body for processing the output signals of the acceleration sensor. FIG. 3 shows a radial acceleration waveform when the test vehicle was operated at a speed of 80 km/hr. FIG. 4 shows frequency spectrums of post-trailing-end waveforms.

The size of the test tire was 315/70R22.5.

Also, two types of vehicles "loaded vehicle" and "half-loaded vehicle" were operated as the test vehicle, and the effects of loading were investigated. The load of the "loaded vehicle" was 2.85 tons, and that of the "half-loaded vehicle" 2.4 tons.

As is clear from FIG. 4, in the frequency spectrums of the post-trailing-end waveforms, the acceleration spectrum level of the unevenly worn tire was higher than that of the normally worn tire in the 800 to 1200 Hz band.

Figure 6A:
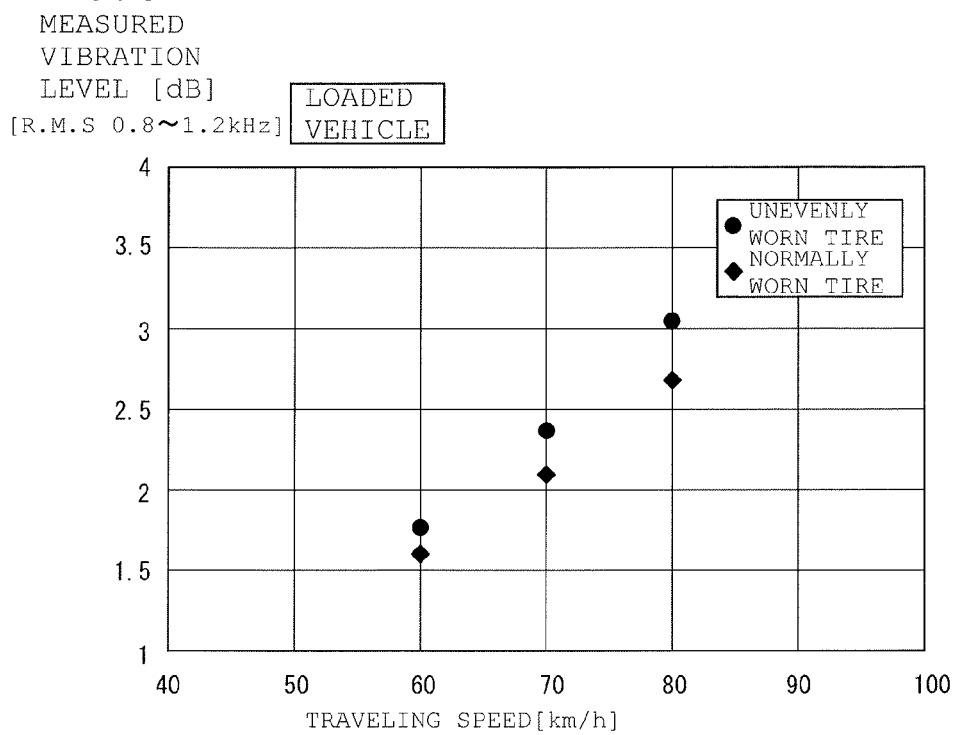
FIG. 6A and FIG. 6B are diagrams showing the relationship between traveling speed and measured vibration level.
Figure 6B:
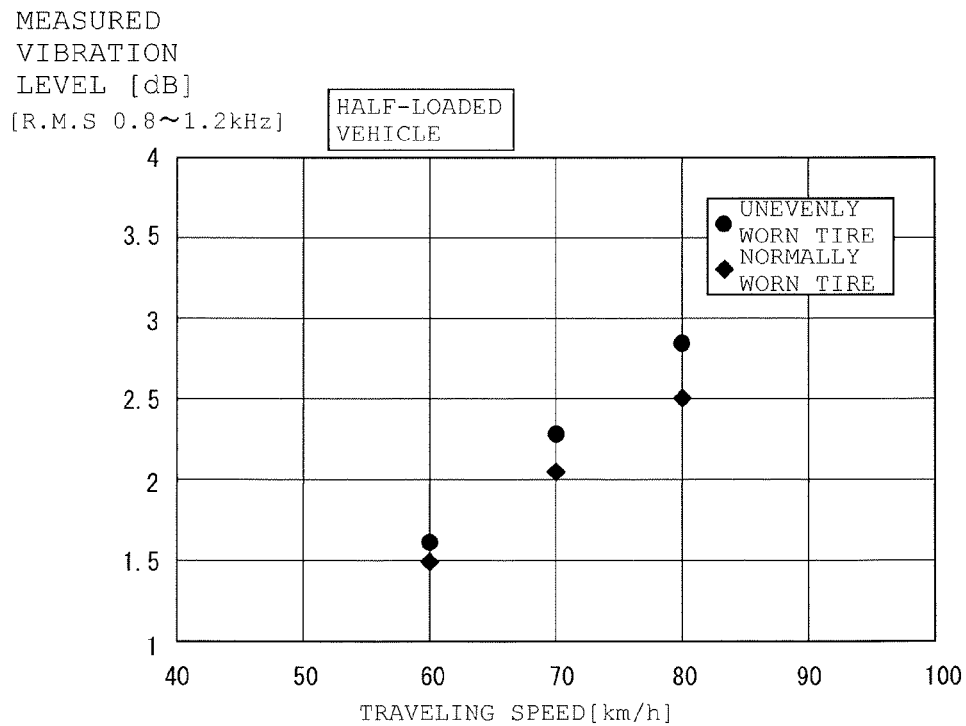

FIGS. 6A and 6B show the relationships between the traveling speeds and the measured vibration levels $\alpha$. FIG. 6A shows the case of measured vibration level $\alpha$ when the load was "loaded vehicle", and FIG. 6B the case of measured vibration level $\alpha$ when the load was "half-loaded vehicle". Whether the loading was "loaded vehicle" or "half-loaded vehicle", it was found that the measured vibration level $\alpha$ of the unevenly worn tire is higher than the measured vibration level $\alpha$ of the normally worn tire.

It is possible to estimate the shoulder edge wear from the level of the measured vibration level $\alpha$. However, as in the present invention, the uneven wear determination index $\gamma$ ($\gamma=\alpha/\beta$), which is the ratio between the measured vibration level $\alpha$ and the reference vibration level $\beta$, or the vibration level in the reference band, may be calculated, and this uneven wear determination index $\gamma$ may be used in determining whether the shoulder edge wear is occurring or not. Then the shoulder edge wear can be estimated with even higher accuracy.

Figure 7A:
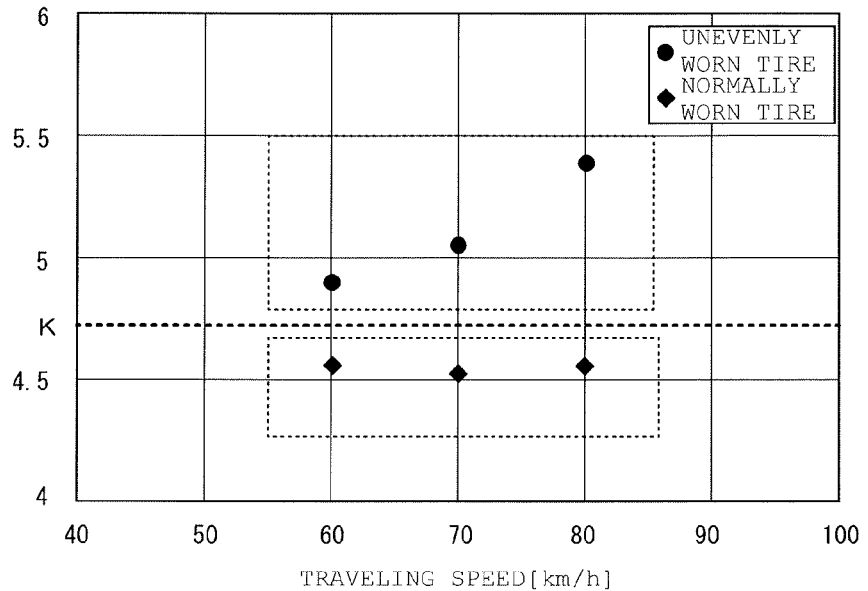
FIG. 7A and FIG. 7B are diagrams showing the relationship between traveling speed and uneven wear determination index.
Figure 7B:
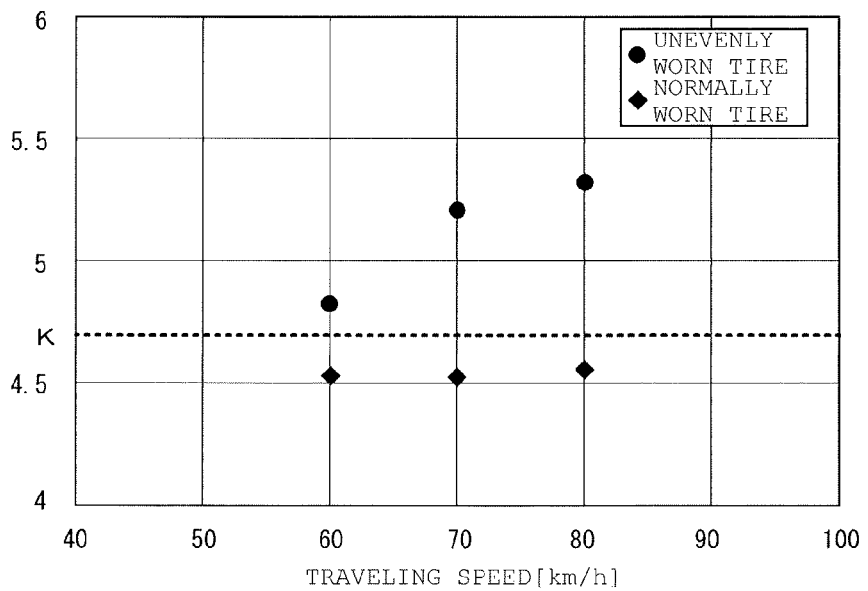

That is, as shown in FIGS. 7A and 7B, the uneven wear determination index $\gamma$ for the normally worn tire is nearly constant whether the load is "loaded vehicle" or "half-loaded vehicle". On the other hand, the uneven wear determination index $\gamma$ for the unevenly worn tire increases with the increase in traveling speed, and is always greater than the uneven wear determination index $\gamma$ for the normally worn tire. Accordingly, a threshold value K can be set independently of traveling speed to determine the occurrence of a shoulder edge wear. This makes it possible to estimate with accuracy whether a shoulder edge wear is occurring or not by comparing the uneven wear determination index $\gamma$ against the threshold value K.

As described above, according to the present invention, the uneven wear determination index $\gamma$ without the effect of traveling speed can be obtained by a simple calculation because the uneven wear determination index $\gamma$ used is $\gamma=\alpha/\beta$.

Also, the occurrence of an uneven (irregular or uneven) wear in an edge of the tire shoulder is determined by comparing the uneven wear determination index $\gamma$ with a threshold value K obtained in advance or the reference determination index $\gamma_0$, which is the uneven wear determination index obtained in advance of a normal tire without the uneven wear. Hence, the occurrence of an uneven wear in an edge of the tire shoulder can be determined with even higher accuracy.

Hereinabove, the present invention has been described by referring to the preferred embodiments and an example. And yet the technical scope of the invention is not limited to the scope as described of the foregoing embodiments and the example. It is apparent to those skilled in the art that various modifications or improvements can be added to the embodiments as described. It is clear from the scope of the appended claims that the embodiments added with such modifications or improvements fall within the technical scope of the present invention.

For example, in the foregoing embodiment, the measured vibration level $\alpha$ and the reference vibration level $\beta$ are derived from the frequency spectrum obtained by applying an FFT processing to the extracted post-trailing-end waveform. However, the R.M.S. average value may be calculated extracting the acceleration waveform containing the 800 to 1200 Hz frequency component only, which is obtained by passing the post-trailing-end waveform through a band-pass filter, and the value may be used as the measured vibration level $\alpha$. At the same time, the R.M.S. average value may be calculated extracting the acceleration waveform containing the 2000 to 2400 Hz frequency component only, which is obtained by passing the post-trailing-end waveform through another band-pass filter, and the value may be used as the reference vibration level $\beta$.

Also, in the foregoing embodiment, the occurrence of a shoulder edge wear is determined by comparing the uneven wear determination index $\gamma$ with the reference determination index $\gamma_0$. However, as in the foregoing example, a threshold value K for the determination of uneven wear may be set in advance, and the threshold value K may be compared with the uneven wear determination index $\gamma$ calculated by the uneven wear determination index calculating means 16. And, if $\gamma>K$, then it may be determined that a shoulder edge wear is occurring.

Also, in the foregoing embodiment, $\alpha/\beta$ is used as the uneven wear determination index $\gamma$, but it is not the limitation. For example, the uneven wear determination index $\gamma$ may be any computed value from $\alpha$ and $\beta$, such as a·$\alpha$−b·$\beta$ (a and b being constants). It is to be noted that the expression for deriving the computed value may be determined as appropriate through experiment or the like.

Also, in the foregoing embodiment, the acceleration sensor 11 is installed radially inside of the center of the central land 3a. However, the acceleration sensor 11 may be installed radially inside of each of the outer lands 3b.

Also, a plurality of acceleration sensors 11 may be installed in positions circumferentially about the tire.

DESCRIPTION OF REFERENCE NUMERALS 1 tire
2 inner liner
3 tire tread
3a central land
3b outer land
3c shoulder land
4a, 4b circumferential groove
10 uneven tire wear estimating apparatus
11 acceleration sensor
12 acceleration waveform extracting means
13 acceleration waveform separating means
14 frequency analyzing means
15 band value calculating means
15a uneven wear measured band value calculating unit
15b reference band value calculating unit
16 uneven wear determination index calculating means
17 storage means
18 determining means

The invention claimed is:

1. A method for estimating uneven tire wear from radial acceleration waveforms detected by an acceleration sensor, the method comprising:

(a) extracting, with a processor, an acceleration waveform in the radial direction of the tire in a post-trailing-end domain from output signals of the acceleration sensor disposed on an inner surface of a tire tread during vehicular travel;

(b) calculating, with the processor, a measured vibration level $\alpha$, which is a level of acceleration in a frequency band of 800 to 1200 Hz, from the extracted acceleration waveform;

(c) calculating, with the processor, a reference vibration level $\beta$, which is a level of acceleration in a frequency band of 2000 to 2400 Hz, from the extracted acceleration waveform;

(d) calculating, with the processor, an uneven wear determination index $\gamma$, which is an index for determining uneven tire wear, from the measured vibration level $\alpha$ and the reference vibration level $\beta$; and (e) determining, with the processor, whether an uneven wear is occurring in an edge of a tire shoulder from a value of the calculated uneven wear determination index $\gamma$.

2. The method for estimating uneven tire wear according to claim 1, wherein the uneven wear determination index is defined by:

$$\gamma = \alpha/\beta.$$

3. The method for estimating uneven tire wear according to claim 1, wherein in step (e), the uneven wear determination index $\gamma$ is compared with a threshold value obtained in advance to determine whether an uneven wear is occurring in an edge of the tire shoulder.

4. The method for estimating uneven tire wear according to claim 1, wherein in step (e), the uneven wear determination index $\gamma$ is compared with a reference determination index $\gamma_0$, which is an uneven wear determination index obtained in advance of a normal tire without uneven wear, to determine whether an uneven wear is occurring in an edge of the tire shoulder.

5. An uneven tire wear estimating apparatus comprising:
an acceleration sensor disposed on an inner surface of a tire tread for measuring acceleration in the radial direction of the tire;
a processor configured to:
extract an acceleration waveform in a post-trailing-end domain from output signals of the acceleration sensor;
calculate a measured vibration level $\alpha$, which is a level of acceleration in a frequency band of 800 to 1200 Hz, from the extracted acceleration waveform;
calculate a reference vibration level $\beta$, which is a level of acceleration in a frequency band of 2000 to 2400 Hz, from the extracted acceleration waveform;
calculate an uneven wear determination index $\gamma$, which is an index for determining uneven wear from the measured vibration level $\alpha$ and the reference vibration level $\beta$; and
determine whether an uneven wear is occurring in an edge of a tire shoulder from a value of the calculated uneven wear determination index $\gamma$.

* * * * *